(12) United States Patent
Afremov et al.

(10) Patent No.: US 6,241,678 B1
(45) Date of Patent: Jun. 5, 2001

(54) SIZING CATHETER FOR MEASURING SEPTAL DEFECTS

(75) Inventors: Michael R. Afremov, St. Louis Park; Kurt Amplatz, St. Paul, both of MN (US)

(73) Assignee: AGA Medical Corporation, Golden Valley, MN (US)

( * ) Notice: Subject to any disclaimer, the term of this patent is extended or adjusted under 35 U.S.C. 154(b) by 0 days.

(21) Appl. No.: 09/137,949

(22) Filed: Aug. 21, 1998

(51) Int. Cl.⁷ ........................................................ A61B 5/02
(52) U.S. Cl. ............................................. 600/481; 600/508
(58) Field of Search ..................................... 600/481, 486, 600/508, 513; 604/48, 54, 96–104; 606/194

(56) References Cited

U.S. PATENT DOCUMENTS

| | | |
|---|---|---|
| 3,095,871 | 7/1963 | Mann et al. . |
| 3,435,826 * | 4/1969 | Fogarty ................................. 606/194 |
| 4,027,659 | 6/1977 | Slingluff . |
| 4,279,252 | 7/1981 | Martin . |
| 4,671,291 | 6/1987 | Wilson . |
| 5,045,072 | 9/1991 | Castillo et al. . |
| 5,255,679 | 10/1993 | Imran . |
| 5,259,837 | 11/1993 | Van Wormer . |
| 5,409,000 | 4/1995 | Imran . |
| 5,451,232 | 9/1995 | Rhinehart et al. . |
| 5,465,732 | 11/1995 | Abele . |
| 5,558,652 | 9/1996 | Henke . |
| 5,591,195 * | 1/1997 | Taheri et al. ....................... 606/194 X |
| 5,632,762 | 5/1997 | Myler . |
| 5,657,764 | 8/1997 | Coulter et al. . |
| 5,683,362 | 11/1997 | Rowland et al. . |
| 5,843,027 * | 12/1998 | Stone et al. ........................ 604/96 X |

* cited by examiner

Primary Examiner—Cary O'Connor
Assistant Examiner—Ryan Carter
(74) Attorney, Agent, or Firm—Nikolai, Mersereau & Dietz, P.A.

(57) ABSTRACT

A sizing catheter and method of measuring a preselected internal opening within a patient to provide a rapid and precise determination of a stretched diameter of the preselected internal opening. The sizing catheter includes a dilation balloon constructed of a thin expandable plastic which is inflatable and is utilized to determine a size of the preselected opening. The dilation balloon is inflated to an inflation threshold, wherein the dilation balloon deforms about the preselected opening and the size of the dilation balloon adjacent the preselected opening approximates a stretched diameter of the preselected opening. The sizing catheter and method may be utilized to determine an appropriate sized occluding device to thereby occlude the preselected opening.

11 Claims, 4 Drawing Sheets

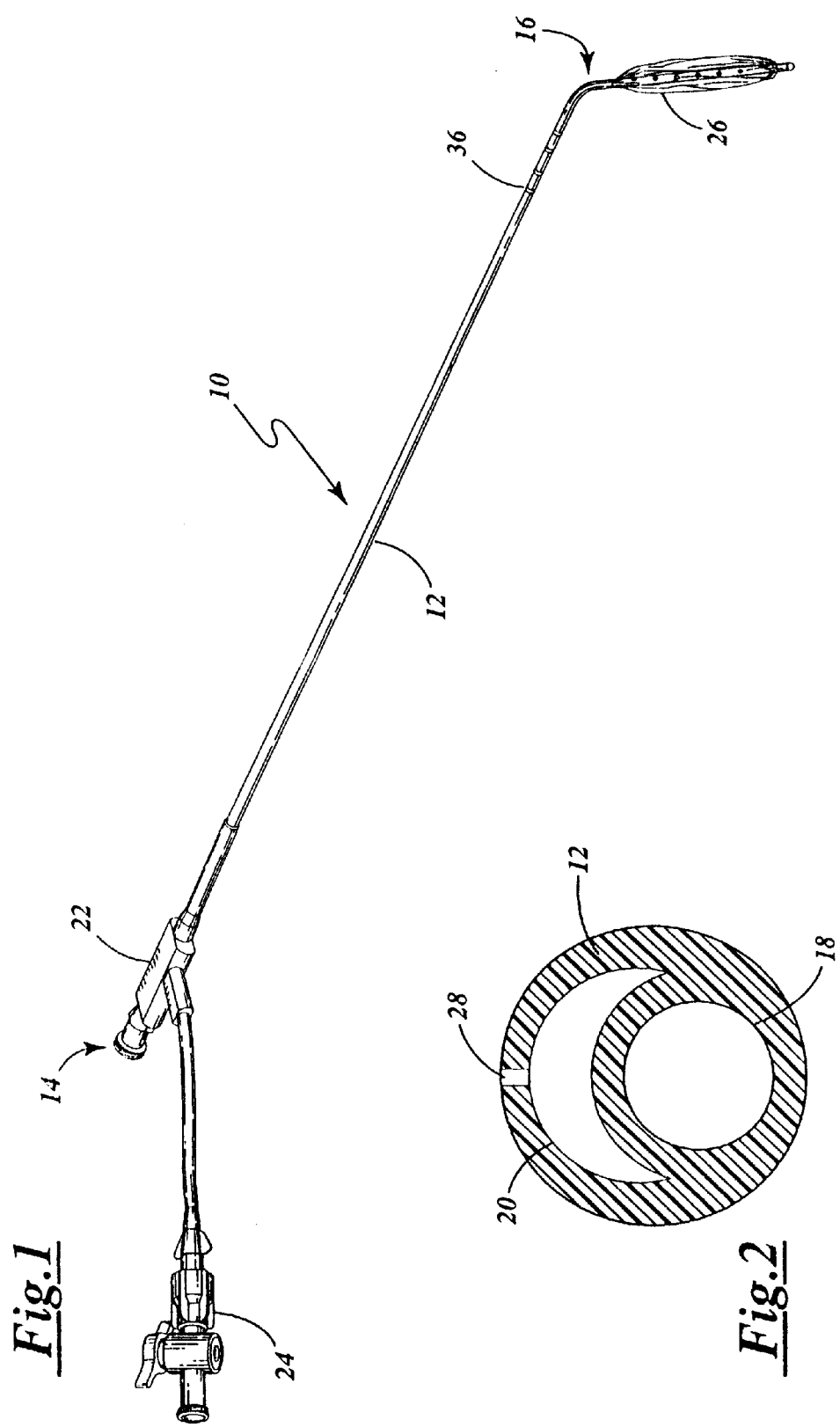

Fig.7

| Model Size(mm) | P. mmHg | Real Size(mm) | Echo Sizing | Difference | Video Sizing | Difference | Cine Sizing | Difference |
|---|---|---|---|---|---|---|---|---|
| 8 | 8 | 7.79 | 7.91 | 0.12 | 7.62 | 0.18 | 7.74 | 0.06 |
| 9 | 10 | 9.09 | 8.94 | 0.15 | 8.65 | 0.44 | 8.41 | 0.69 |
| 10 | 15 | 9.93 | 9.45 | 0.48 | 9.71 | 0.23 | 9.24 | 0.69 |
| 11 | 43 | 11.22 | 10.8 | 0.42 | 10.75 | 0.47 | 10.46 | 0.77 |
| 12 | 50 | 11.92 | 11.5 | 0.42 | 11.72 | 0.2 | 11.52 | 0.4 |
| 13 | 68 | 12.72 | 13.6 | 0.88 | 12.54 | 0.18 | 12.2 | 0.53 |
| 14 | 70 | 14.65 | 14.5 | 0.15 | 14.19 | 0.47 | 13.94 | 0.71 |
| 15 | 88 | 15.17 | 16.5 | 1.33 | 15.08 | 0.1 | 14.47 | 0.7 |
| 16 | 93 | 16.03 | 18 | 1.97 | 16.12 | 0.09 | 15.45 | 0.58 |
| 17 | 95 | 16.8 | 16.9 | 0.1 | 16.87 | 0.07 | 16.21 | 0.18 |
| 18 | 100 | 18.28 | 17.3 | 0.98 | 18.71 | 0.43 | 17.74 | 0.54 |
| 20 | 120 | 19.88 | 19.7 | 0.18 | 20.33 | 0.45 | 19.35 | 0.53 |
| 22 | 140 | 22.3 | 22.1 | 0.2 | 22.74 | 0.44 | 21.86 | 0.45 |
| 24 | 180 | 24.05 | 23.6 | 0.45 | 24.68 | 0.63 | 23.31 | 0.74 |
| 26 | 200 | 25.65 | 26.2 | 0.55 | 26.94 | 1.29 | 24.84 | 0.81 |
| 28 | 280 | 27.06 | 25.9 | 1.16 | 28.55 | 1.49 | 26.13 | 0.93 |
| 30 | 325 | 30.28 | 29 | 1.28 | 32.1 | 1.82 | 29.52 | 0.77 |
| | | | | average 0.64 | | average 0.53 | | average 0.59 |
| | | | | SD: 0.54 | | SD: 0.52 | | SD: 0.23 |
| | | | RSQ: 0.98470314 | | RSQ: 0.99886697 | | RSQ: 0.99932096 | |

SIZING CATHETER FOR MEASURING SEPTAL DEFECTS

BACKGROUND OF THE INVENTION

I. Field of the Invention

The present invention relates generally to a device and non-surgical method for determining the size of an internal opening within a patient. More particularly, the present invention relates to a sizing catheter and method of using the same, wherein the sizing catheter may be utilized to determine the stretched diameter of an internal passage within a patient. The sizing catheter of the present invention is particularly well suited for determining the stretched diameter of a defect, such as a septal defect, within the heart of a patient. Once the stretched diameter of the defect is known, a properly sized occluding device may be selected and positioned within the opening of the defect.

II. Description of the Related Art

Over the years various medical devices, including stents and occluders, have been developed for placement within a preselected internal passage, opening, or defect of a patient. Complex devices may be delivered and used in treating specific abnormal conditions, such as devices used in removing vascular occlusions or devices used in treating septal defects and the like. Through advancement in a variety of devices, stents and occluders may be delivered non-surgically. Certain intravascular devices, such as catheters and guide wires, may be used to deliver certain medical devices to a specific location within a patient's heart, for example. Further, a catheter may be used to reach a selected coronary artery within the vascular system or a catheter and/or guidewire may be used to deliver a device to an interior chamber of the patient's heart.

Prior to delivering the particular medical device, the size of the internal passage, opening or defect must be determined in order that an appropriately sized device may be provided. Further, determination of the "stretched diameter" of the opening or defect is desirable to provide a preferred fit between the medical device and the surrounding tissue. In the past, physicians have utilized a balloon catheter in an attempt to determine the size of the internal opening or defect. Typically, the physician will position the balloon within the opening and slowly inflate the balloon, pushing or pulling the balloon of the catheter fore or aft until the physician feels resistance against the balloon. The size of the balloon corresponding with the size of the opening is then determined. The technique of pulling or pushing a balloon catheter through the opening or defect is unreliable and does not determine the size of the opening when the surrounding tissue is stretched.

A balloon catheter and a calibrated guidewire having radiopaque regions of known length, may be utilized by a physician during a preliminary fluoroscopic procedure to estimate the defect's size, shape and thickness of the septal wall near the defect. Although useful, the defects exact size when stretched and the shape cannot be determined, thereby increasing the possibility of leakage around the device.

Echocardiography has also been used to estimate the diameter of the opening or defect, however, echo measurements are always significantly smaller than the "stretched diameter". The differences between echo measurements and stretched diameters may range between 2 mm to 10.5 mm. It has been suggested that the stretched diameter can be estimated from echo measurements by multiplying 1.05 times the echo measurement and then adding 5.49. Although this formula may prove sufficient in some cases, differences of up to 4.5 mm between the actual stretched diameter and the estimated diameter from this formula have been observed. The errors in echo measurements can be explained by the fact that most communications are not perfectly round whereas the balloon transforms the deformed communication into a round structure. If a device is selected which is too small, the risk of embolization and residual shunting increases significantly. On the other hand, if the device is too large, the device may not fit properly within the opening or defect.

Other methods have been described for determining the size of the internal opening utilizing a balloon catheter. For example, Taheri et al. in U.S. Pat. No. 5,591,195 describes a sizing catheter, wherein the pressure within an inflatable balloon is measured. Taheri et al. teaches that when the balloon makes contact with a vessel to be measured, the pressure within the balloon increases. The size of the balloon may then be determined from a chart of known balloon pressures and diameters. As seen in FIG. 9, the pressure within the balloon may vary even though the actual diameter being measured remains the same. A need therefore exists for a device that can determine the stretched diameter of an internal passage, opening or defect. The present invention meets these and other needs which will become apparent to those skilled in the art.

SUMMARY OF THE INVENTION

The purpose of the present invention is to provide a device and method for determining the nominal and/or "stretched diameter" of an internal opening or defect within a patient. Those skilled in the art will appreciate that the device and method of the present invention may be utilized to determine the size of any of several defects, passages, or internal openings within a patient. For ease of discussion, and without any limitation intended, the device and method of the present invention will be described in conjunction with determining the stretched diameter of a septal defect within the heart of a patient.

The device and method of the present invention may be utilized in conjunction with radiology, fluoroscopy, echocardiography, and/or other known suitable means for viewing the distal end of a catheter positioned within a patient's heart. The sizing catheter of the present invention includes a tubular shaft having a longitudinal axis extending between a proximal end and a distal end of the tubular shaft. The tubular shaft has one or more lumens formed within the tubular shaft, wherein the lumens are adapted for receiving, for example, a guidewire, device, pressurized fluid, etc. One of the lumens extends between the proximal end and a region short of the distal end of the tubular shaft and terminates into a series of ports extending through the tubular shaft from the lumen to an outer surface of the tubular shaft. The series of ports may be aligned in a spiral fashion around the circumference of the tubular shaft. An elongated dilation balloon is affixed to the tubular shaft proximate the distal end of the tubular shaft and encloses the series of ports.

The dilation balloon is constructed of a thin expandable plastic having an inflation threshold which corresponds with the stretchability of the tissue of the defect. In use, when the dilation balloon is positioned within the predetermined opening and inflated, the dilation balloon resists deformation up to the inflation threshold, thereby causing the tissue surrounding the opening to stretch. Once the inflation threshold is reached, the dilation balloon deforms about the predetermined opening, such that a noticeable waist of the balloon is formed adjacent the predetermined opening. Markings on the distal end of the catheter having known separation distances may be utilized to determine a size of the dilation balloon adjacent the predetermined opening, thereby assisting in the determination of the stretched diameter of the predetermined opening.

Alternatively, when the inflation threshold is reached and the dilation balloon deforms, the pressure within the dilation balloon may be noted. The catheter may then be removed from the heart and the distal end inserted in a template having apertures of known dimension. The balloon may then be inflated to the noted pressure within an aperture estimated to be larger than the stretched diameter of the septal defect. If the balloon deforms, the selected aperture in the template may approximate the stretched diameter of the septal defect. The next size larger aperture may be tested to verify that the balloon does not deform in this larger aperture. If the balloon does not deform in the first selected aperture, then the next smaller aperture in the template is selected and the balloon is inflated to the noted pressure. If the balloon deforms in this aperture, the dimension of the aperture corresponds with the stretched diameter of the opening. This procedure is repeated until the balloon deforms within an aperture at the noted pressure. In this manner, the stretched diameter of the defect or passage may be determined.

In order to increase the likelihood that the distal end of the catheter extends through the defect perpendicular to the plane of the defect, the distal end of the tubular shaft may be preset with a 45 degree bend relative to the longitudinal axis of the tubular shaft. Those skilled in the art will appreciate that an angulation of 45 degrees relative to the longitudinal axis of the tubular shaft is preferable because the average atrial septum of the heart has a 45 degree inclination. Also, such orientation is preferrable when using the radiopaque markings to estimate distances and sizes within the heart.

OBJECTS

It is accordingly a principal object of the present invention to provide a device and method for non-evasively determining the size of a stretched internal passage or defect.

Another object of the present invention is to provide a device suitable for use in determining a properly sized occluding device for use occluding a defect.

These and other objects, as well as these and other features and advantages of the present invention will become readily apparent to those skilled in the art from a review of the following detailed description of the preferred embodiment in conjunction with the accompanying claims and drawings in which like numerals in the several views refer to corresponding parts.

BRIEF DESCRIPTION OF THE DRAWINGS

FIG. 1 is a perspective view of a sizing catheter of the present invention;

FIG. 2 is a partial sectional end elevational view of the catheter body of the present invention;

FIG. 7 is a chart demonstrating differences in the accuracy of determining the inflated size of the balloon of the sizing catheter of the present invention for several measuring means.

DETAILED DESCRIPTION OF THE PREFERRED EMBODIMENT

Figure 3:
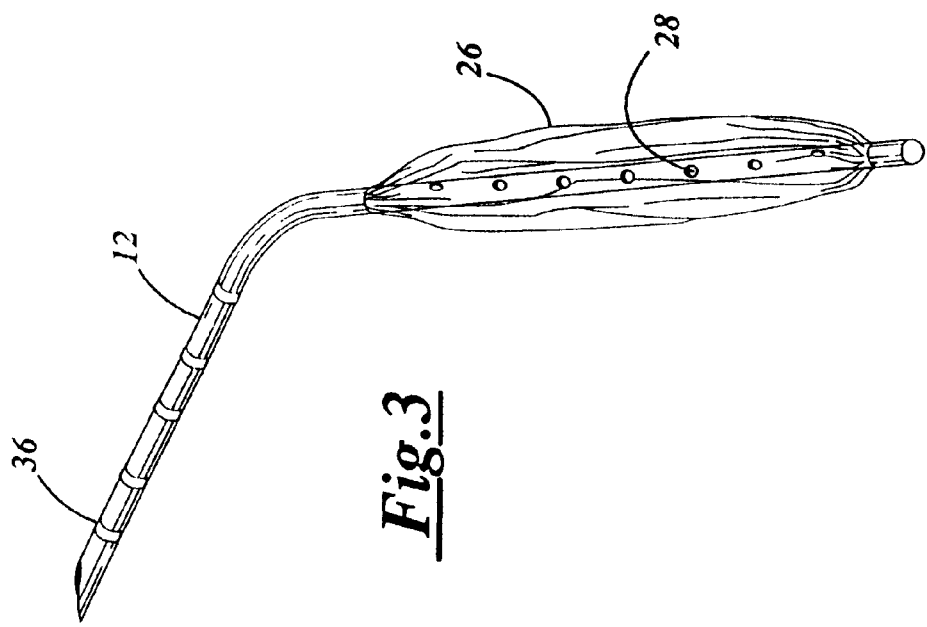
FIG. 3 is a fragmented perspective view of the distal end of the sizing catheter of the present invention.

Referring first to FIG. 1 there is shown generally a sizing catheter 10 for measuring the size of a passage, opening, or defect. The sizing catheter 10 includes a tubular shaft 12 having a longitudinal axis extending between a proximal end 14 and a distal end 16 and includes a first and second lumen 18 and 20 formed therein. The proximal end includes a guidewire connector 22 and pressure valve assembly 24 coupled thereto. Without any limitation intended, in the preferred embodiment the first lumen 18 is adapted for receiving a guidewire (not shown) therein. The second lumen 20 is formed within the tubular shaft 12 and extends between the proximal end 14 of the tubular shaft 12 to a region short of the distal end 16 and terminates into a series of ports 28 extending through the tubular shaft 12 from the lumen 20 to an outer surface of the tubular shaft 12 (see FIG. 2). An elongated dilation balloon 26 is affixed to the tubular shaft 12 proximate the distal end of the tubular shaft and encloses the series of ports 28 (see FIG. 3). The second lumen 20 serves as a conduit between the balloon 26 and a means of known suitable construction for increasing the pressure within lumen 20 which is coupled to the pressure valve assembly 24. The first lumen 18 of the sizing catheter 10 may be sized for passage over a 0.035 inch guidewire, leaving room for a relatively large second lumen 20 for rapid inflation and deflation of the balloon 26.

The dilation balloon 26 is constructed of a thin expandable plastic having an inflation threshold, such that when the dilation balloon 26 is positioned and inflated within a predetermined opening, the dilation balloon resists deformation up to the inflation threshold. Without any limitation intended, in the preferred embodiment the tubular shaft may be constructed of a known suitable radiopaque nylon based polymer composite and the balloon 26 may be constructed of a 2 mil thick expandable polymer such as a polyurethane membrane. Once the dilation threshold is reached, the dilation balloon 26 deforms about the predetermined opening. A size of the dilation balloon adjacent the predetermined opening approximates a stretched diameter of the predetermined opening.

Figure 4:
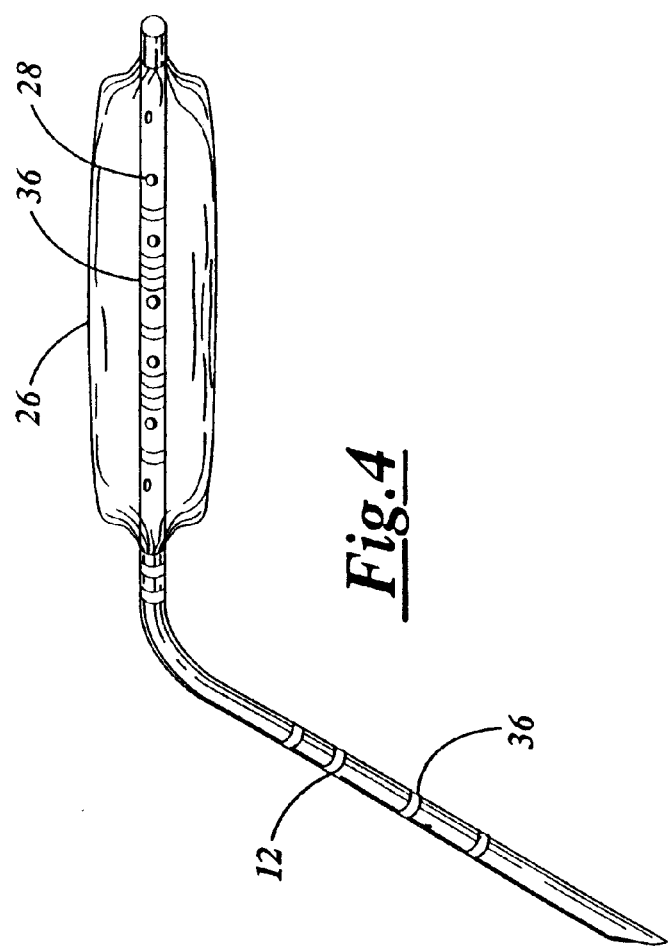
FIG. 4 is a fragmented perspective view of the distal end of the sizing catheter of the type shown in FIG. 3 with the balloon inflated.

Referring to FIG. 4, the distal end 16 of the sizing catheter 10 is shown. Radiopaque markings 36 of known suitable construction may be affixed or formed on the tubular shaft 12 proximate the dilation balloon 26. The distal end 16 of the tubular shaft 12 is bent at a 45 degree angle relative to the longitudinal axis of the tubular shaft. In this manner the longitudinal axis of the distal end 16 of the sizing catheter 10 may be positioned perpendicular to the plane of the predetermined opening.

Figure 5:
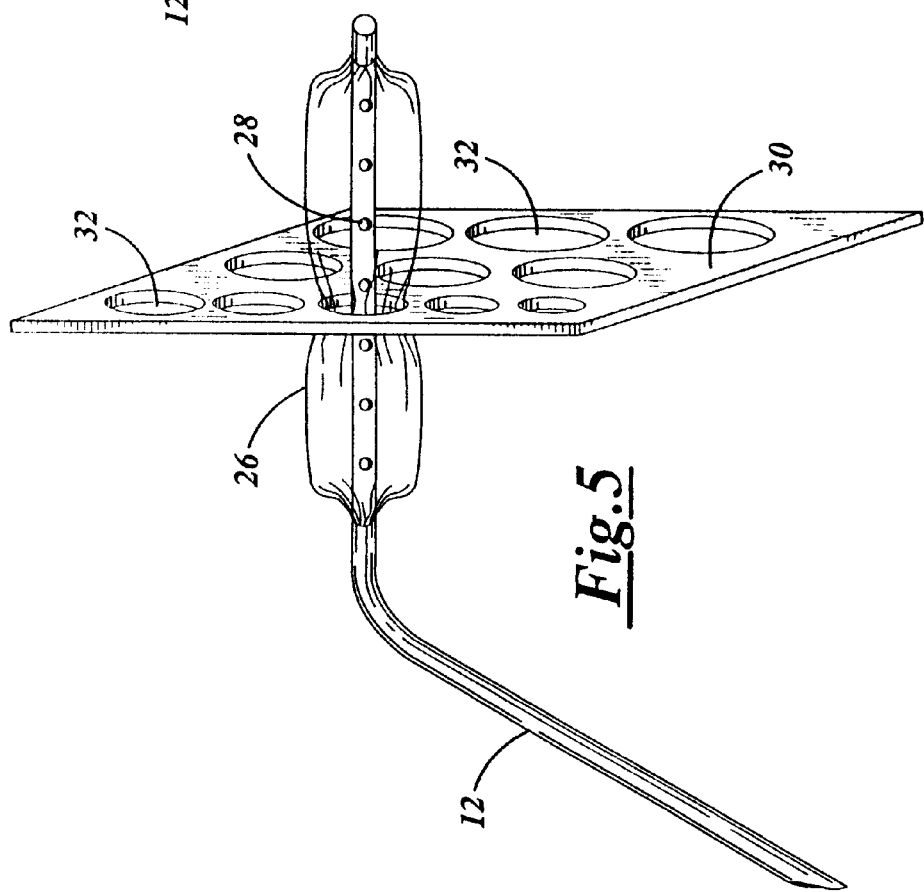
FIG. 5 is a fragmented perspective view of the distal end of the sizing catheter of the type shown in FIG. 3 with the balloon inflated and positioned within an aperture of a sizing template.

Referring to FIG. 5, the distal end 16 of the sizing catheter 10 is shown positioned within an aperture 32 of template 30 with the balloon 26 inflated above the inflation threshold. Various sized apertures 32 of known dimension are formed in the template 30. As further described below, the pressure within the balloon inflated to the inflation threshold varies depending upon the size of the aperture 32.

Figure 6:
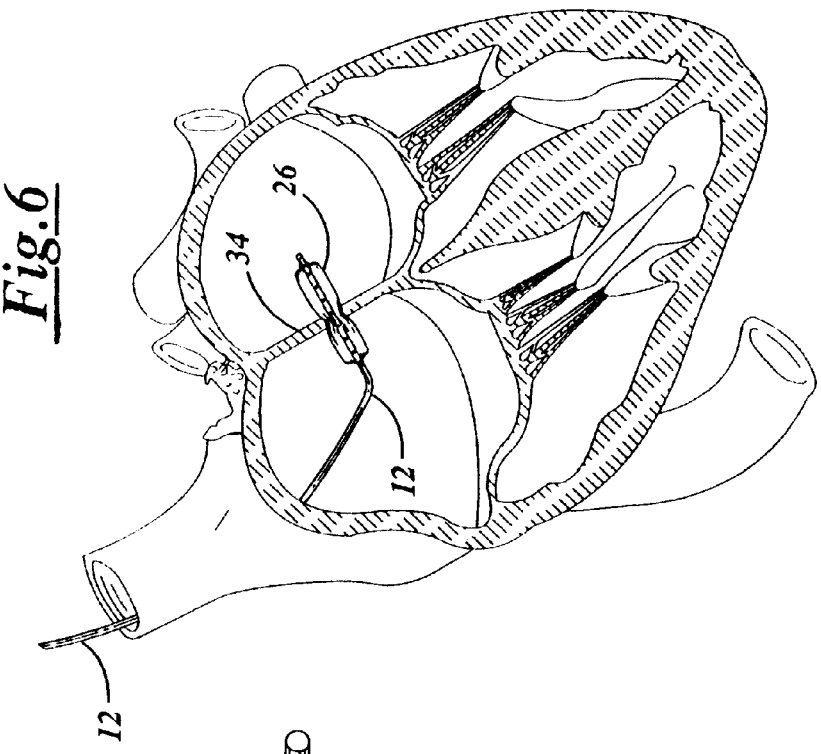
FIG. 6 is a fragmented perspective view of the distal end of the sizing catheter of the type shown in FIG. 3 with the balloon inflated and positioned within a septal defect of a heart.

Having described the constructional features of the present invention, the mode of use will next be described in conjunction with FIGS. 6 and 7. Those skilled in the art will appreciate that the device and method of the present invention may be utilized to determine the size of any of several defects, passages, or internal openings within a patient, however, for ease of discussion, and without any limitation intended, the mode of use will be described in conjunction with determining the stretched diameter of a septal defect within the heart of a patient. In the preferred embodiment, although it may not be necessary, prior to inserting the catheter within the patient, the balloon 26 is inflated with carbon dioxide and then all gases are aspirated from the second lumen 20.

After the hemodynamic data of the patient is obtained, an introducing catheter is passed through the atrial communication into one of the left pulmonary veins and an exchange guidewire is introduced. The introducing catheter and sheath are then removed and the sizing catheter 10 is passed over the exchange guidewire directly through the skin. To facilitate this percutaneous entry, an assistant applies forceful negative pressure with an attached syringe. Under fluoroscopic and echocardiographic guidance, the distal end 16 of the sizing catheter 10 is positioned across the defect. The balloon 26 is then inflated with diluted contrast medium until a waist can be observed (the inflation threshold is reached) and/or left-to-right shunting ceases as observed by Doppler echocardiography. The diameter of the balloon 26 adjacent the defect may then be determined by many of several known means including echocardiography or radiology. Referring to the chart shown in FIG. 7, it is anticipated that echo measurements will suffice, however, x-ray measurements can be added. Further, if desired, the sizing catheter 10 may be removed, and positioned within various apertures of template 30. The balloon is re-inflated with the same known amount of contrast medium, and it may be determined which aperture corresponds with the same deformation of the balloon 26 observed within the defect. Once the stretched diameter of the septal defect is determined, a properly sized occluding device may be selected positioned within the defect.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself

What is claimed is:

1. A sizing catheter for measuring the size of an intracardiac opening, said sizing catheter including: a tubular shaft having a longitudinal axis extending between a proximal end and a distal end thereof, said tubular shaft further having a lumen extending between the proximal end and a region short of the distal end and terminating into a series of ports extending through the tubular shaft from the lumen to an outer surface of the tubular shaft, wherein an elongated dilation balloon affixed to the tubular shaft proximate the distal end of the tubular shaft encloses the series of ports, said dilation balloon being constructed of a thin expandable plastic and having an inflation threshold, wherein when the dilation balloon is positioned within a predetermined opening and inflated, said dilation balloon resists deformation up to the inflation threshold such that when the inflation threshold is reached the dilation balloon deforms about the predetermined opening and a size of the dilation balloon adjacent the predetermined opening approximates a stretched diameter of the predetermined opening.

2. The sizing catheter as recited in claim 1, further including radiopaque markings affixed to the tubular shaft proximate the dilation balloon.

3. The sizing catheter as recited in claim 1, wherein the distal end of the tubular shaft is bent at a 45 degree angle relative to the longitudinal axis of the tubular shaft.

4. The sizing catheter as recited in claim 1, wherein the dilation balloon is constructed of an expandable polymer.

5. The sizing catheter as recited in claim 1, wherein the dilation balloon is constructed of polyurethane.

6. The sizing catheter as recited in claim 1, wherein the series of ports are aligned in a spiral fashion around the circumference of the tubular shaft.

7. A method of determining a size of an intracardiac opening, said method including the steps of:

a) providing a sizing means for sizing a predetermined internal opening of a patient, said sizing means including an elongated dilation balloon being constructed of a thin expandable plastic and being inflatable to thereby approximate a size of the predetermined opening;

b) providing a viewing means for viewing the internal position of the elongated dilation balloon positioned within a patient's body;

c) positioning the dilation balloon of the sizing means within the predetermined opening;

d) inflating said dilation balloon to an inflation threshold, such that the dilation balloon deforms about the predetermined opening and a size of the dilation balloon adjacent the predetermined opening approximates a stretched diameter of the predetermined opening; and e) determining the size of the dilation balloon adjacent the predetermined opening.

8. The method as recited in claim 7, wherein the step of positioning the dilation balloon further includes positioning a longitudinal axis of the balloon relatively perpendicular to a plane of the predetermined opening.

9. The method as recited in claim 7, wherein said sizing means includes markers viewable by said viewing means, wherein said sizing means is advanced through the predetermined opening such that said markers may be utilized to determine a thickness dimension of the predetermined opening.

10. The method as recited in claim 8, wherein said sizing means includes markers viewable by said viewing means, wherein said sizing means is advanced through the predetermined opening such that said markers may be utilized to determine a thickness dimension of the predetermined opening.

11. The method as recited in claim 7, wherein the viewing means utilizes echocardiography to view the internal position of the elongated dilation balloon.

* * * * *